US00PP19630P3

(12) United States Plant Patent
Russell et al.

(10) Patent No.: US PP19,630 P3
(45) Date of Patent: Jan. 20, 2009

(54) PLUM TREE NAMED 'QUEEN GARNET'

(50) Latin Name: *Prunus salicina Lindl*
Varietal Denomination: Queen Garnet

(75) Inventors: Dougal Mackenzie Russell, Brisbane (AU); Bruce Topp, Coes Creek (AU)

(73) Assignee: State of Queensland through its Department of Primary Industries and Fisheries, Brisbane (AU)

( * ) Notice: Subject to any disclaimer, the term of this patent is extended or adjusted under 35 U.S.C. 154(b) by 0 days.

(21) Appl. No.: 11/804,485

(22) Filed: May 18, 2007

(65) Prior Publication Data

US 2008/0289071 P1 Nov. 20, 2008

(51) Int. Cl.
*A01H 5/00* (2006.01)

(52) U.S. Cl. ..... Plt./184

(58) Field of Classification Search ..... Plt./184
See application file for complete search history.

*Primary Examiner*—Annette H Para
(74) *Attorney, Agent, or Firm*—Davis Wright Tremaine LLP

(57) ABSTRACT

A new and distinct plum tree variety bearing fruit which are high in antioxidants and anthocyanins that makes it distinct from other Japanese-like plum trees that bear red fleshed fruit. The fruit is characterized by its attractive dark red to black skin color and its intense blood red flesh color ripening in mid February in the Granite Belt of southern Queensland, Australia. The trees are precocious with regular high annual fruit production.

4 Drawing Sheets

Latin name of the genus and species of the plant claimed: *Prunus salicina Lindl.*
Variety denomination: 'Queen Garnet'.

BACKGROUND AND SUMMARY OF THE INVENTION

This invention relates to the discovery and asexual propagation of a new and distinct variety of plum tree, *Prunus salicina Lindl* cv. 'Queen Garnet', as herein described and illustrated.

The new plum tree variety originated from the Queensland Department of Primary Industries and Fisheries stone fruit breeding program at the Applethorpe Research Station from an open pollination of 'Blackamber' (unpatented) plum and 'Amber Jewel' (unpatented) plum. Seeds were collected, germinated and planted as seedlings on their own roots at the Applethorpe Research Station in October, 1998. The new plum tree variety was selected in 2001, and has been tested as 'GB 403-39' (hereinafter to be referred to as 'Queen Garnet'). The new plum tree variety 'Queen Garnet' was first asexually propagated by budding onto 'Nemared' and 'Golden Queen' (unpatented) peach rootstocks in 2001 in an experimental orchard at the Applethorpe Research Station for two succeeding generations, which shows that characteristics of the tree are established and uniformly transmitted.

The new and distinct variety of plum tree is characterised by a medium-large tree that is precocious and productive. The new plum tree variety 'Queen Garnet' is self-unfruitful and blooms early to mid-season with 'Blackamber' and 'Santa Rosa' (unpatented), both of which are adequate pollinisors. Fruit of the new plum tree variety 'Queen Garnet' are medium to large, black skinned with extremely dark red flesh that is firm, almost non-melting in texture, and moderately sweet flavour. The fruit of the new plum tree variety 'Queen Garnet' mature in Stanthorpe, Queensland, Australia in mid February, about two weeks later than 'Friar' (unpatented) and 'Amber Jewel' plum depending on seasonal conditions. Further, the fruit of the new plum tree variety 'Queen Garnet' are extremely high in anthocyanins that make it distinct from other red fleshed plums.

Contrast is made to 'Donsworth' (unpatented) plum for reliable description and contrast.

The new plum tree variety 'Queen Garnet' is distinct from its seed parent 'Blackamber' inter alia by producing fruit having flesh that tends to be a dark red. In contrast, 'Blackamber' produces fruit having flesh that tends to be amber. The new plum tree variety 'Queen Garnet' also resembles 'Mariposa' (unpatented) but it is distinguished from 'Mariposa' inter alia by producing fruit having high total antioxidant capacity. In contrast, 'Mariposa' produces fruit having low to moderate antioxidant capacity.

The new plum tree variety is moderately vigorous and large, and semi-spreading in growth with adaptation to high chill stonefruit production regions producing annual crops of good flavour and eating quality fruit of medium to large size, semi-freestone fruit with full dark red to black skin and dark, blood red flesh with extremely high levels of anthocyanin compounds which ripen about 2 weeks later than 'Friar' in mid-February and having firm flesh with good shipping characteristics for its intended fresh market use.

BRIEF DESCRIPTION OF THE PHOTOGRAPHS

The accompanying photographic illustrations show typical specimens in full colour of the foliage and fruit of the new plum tree variety named 'Queen Garnet'. The colours are as nearly true as is reasonably possible in a colour representation of this type.

DETAILED BOTANICAL DESCRIPTION OF THE INVENTION

Figure 1:
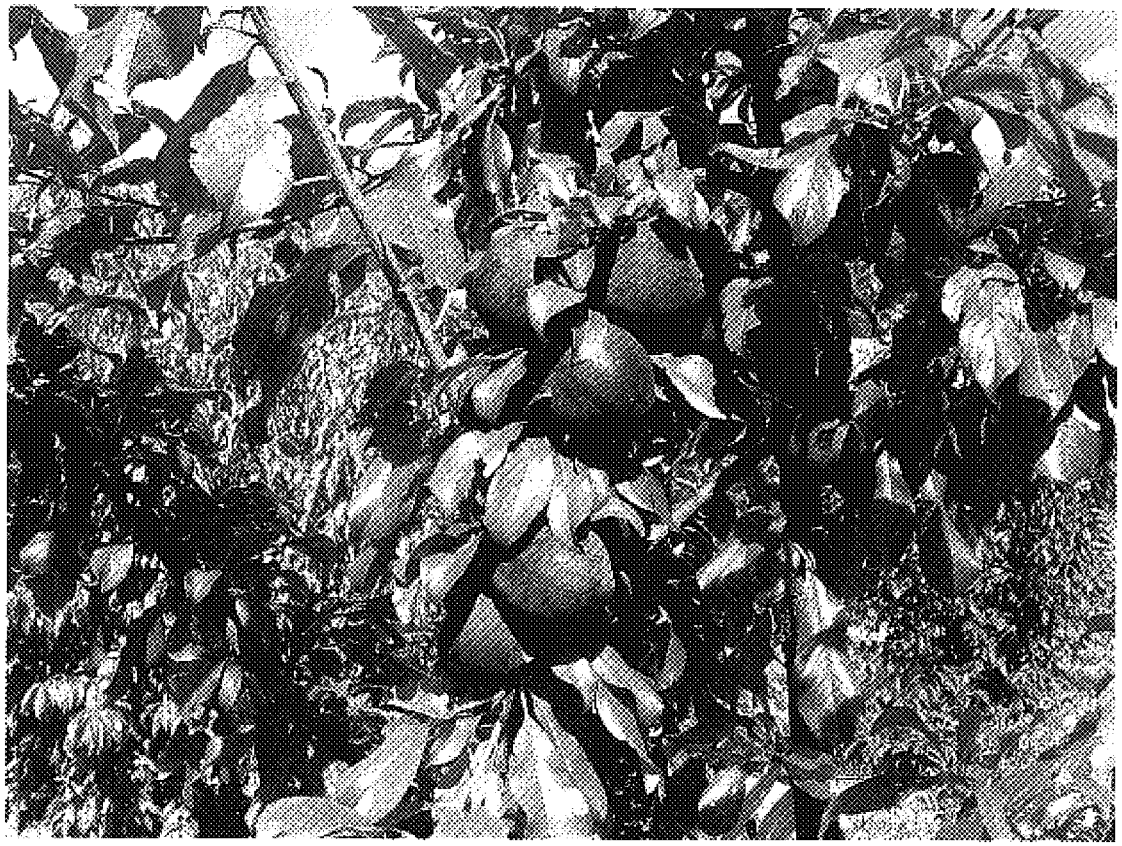
FIG. 1 is a photographic representation showing the fruit of the new plum tree variety named 'Queen Garnet' clustered on fruiting branches prior to harvest.
Figure 2:
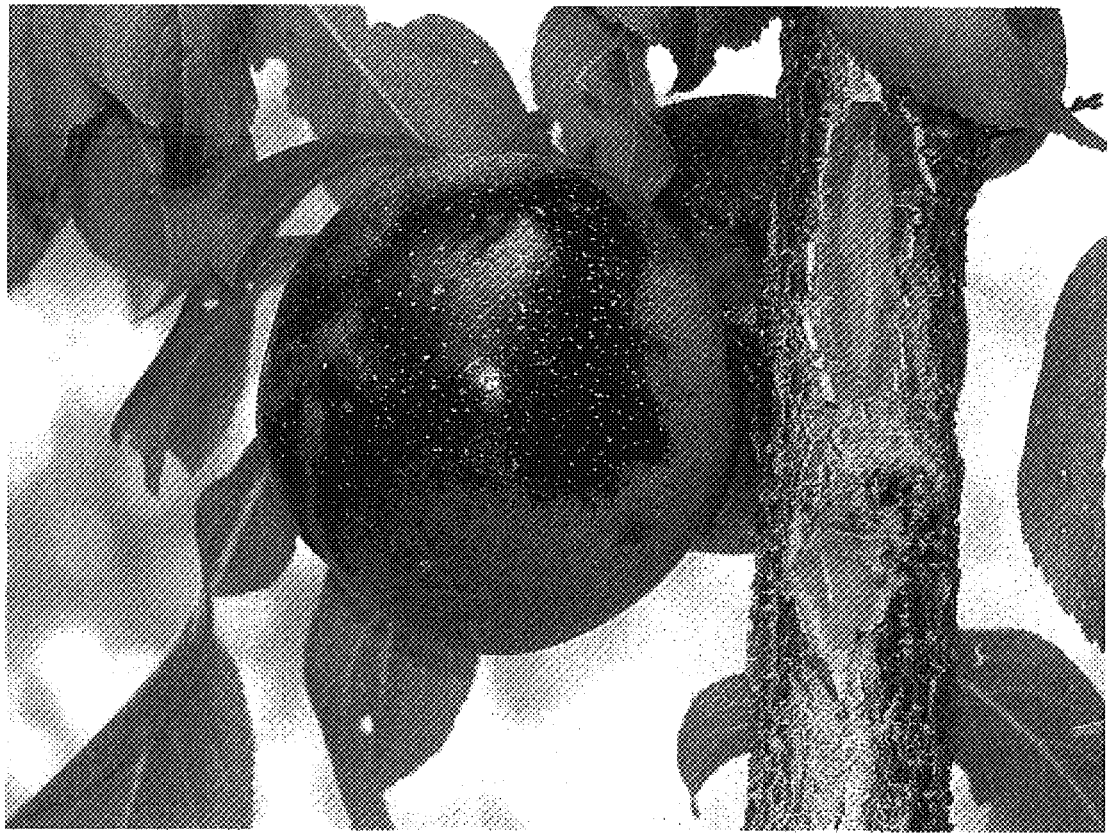
FIG. 2 is a photographic representation showing an individual cluster of the fruit of the new plum tree variety 'Queen Garnet' with part of the natural fruit blush wiped off to show underlying skin colour and fruit lenticels.
Figure 3:
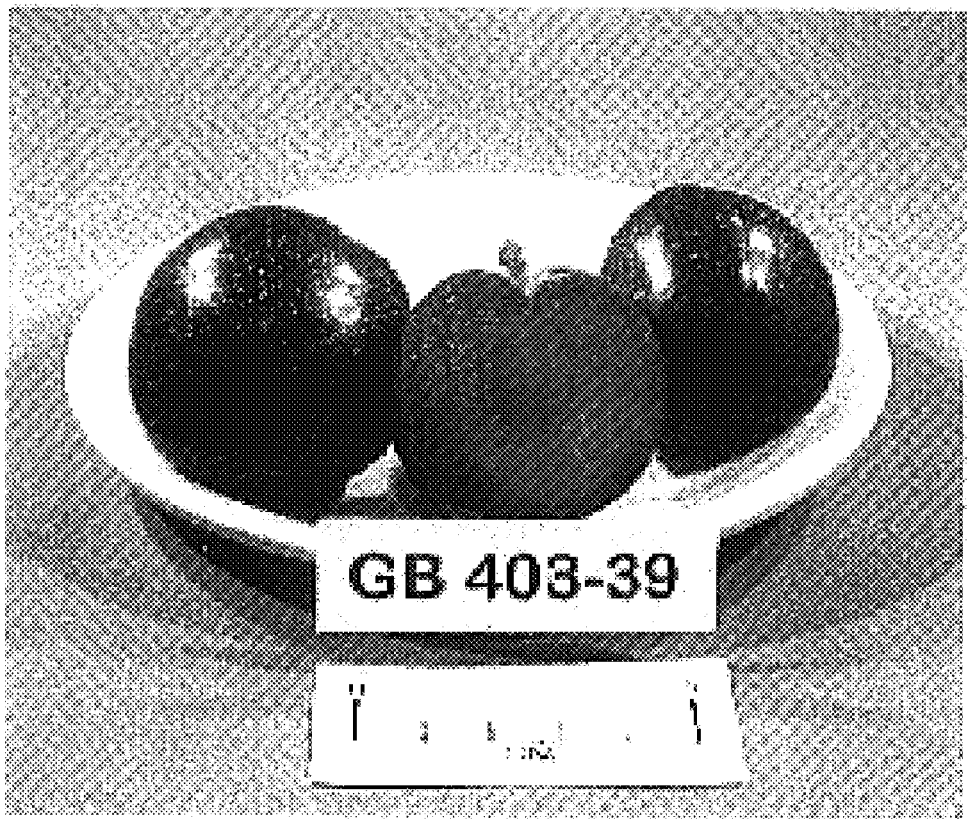
FIG. 3 is a photographic representation showing a group of fruit harvested from the new plum tree variety 'Queen Garnet'.
Figure 4:
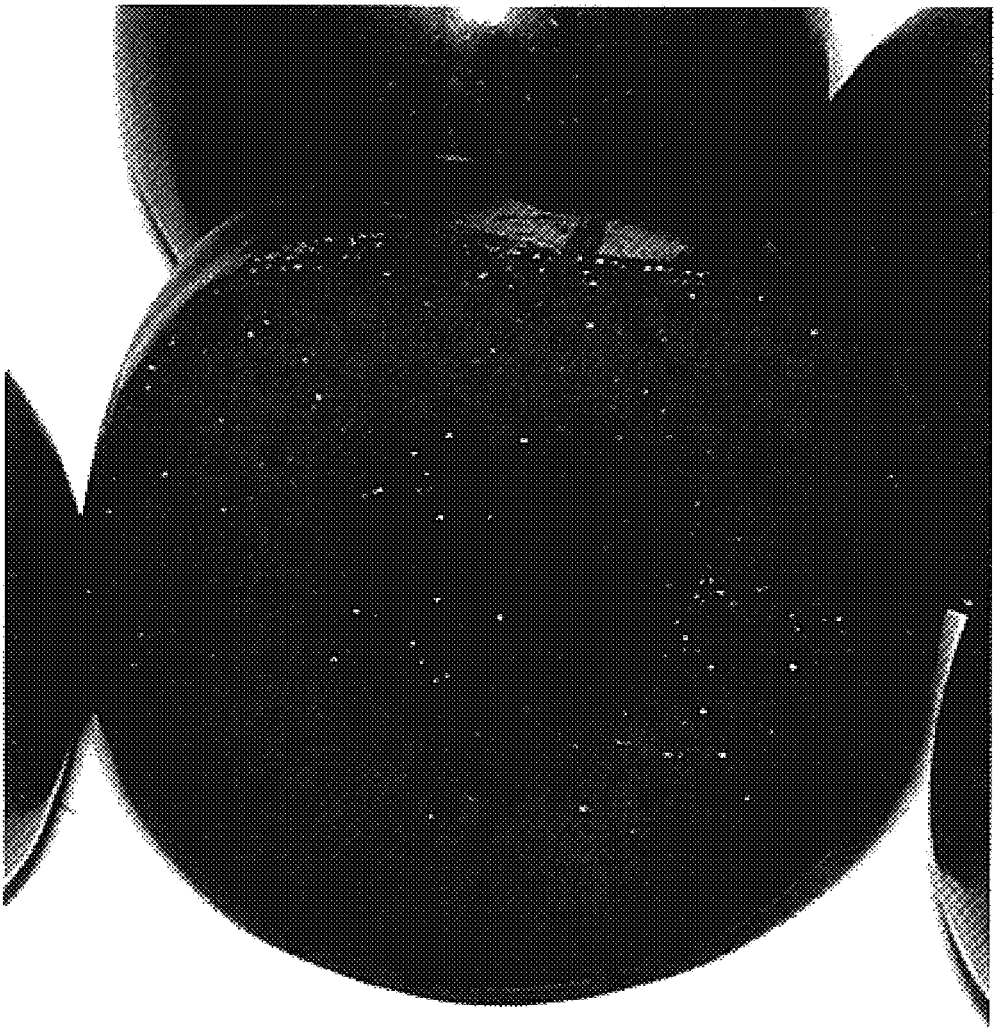
FIG. 4 is a photographic representation showing a close-up of a cut surface of the fruit of the new plum tree variety 'Queen Garnet', which appears as dark, blood red flesh.

Throughout this specification, colour names beginning with a small letter signify that the name of that colour, as used in common speech, is aptly descriptive. Colour names (except those in common terms) with name, number and capital letter designate values based upon The Royal Horticultural Society (R.H.S.) Colour Chart 1966, LONDON, Flower Council of Holland.

The new plum tree variety described herein was derived from an open-pollinated cross of 'Blackamber' plum (female (seed) parent) and the Australian plum variety 'Amber Jewel' (male (pollen) parent). Fruit were first picked and observed in January 2001, then asexually propagated onto peach rootstock ('Nemared' peach) and subsequently observed on top-worked peach trees in late January 2004.

All observations subsequently have been on the original tree and grafted trees of the new plum tree variety 'Queen Garnet'. Asexual reproduction of this new variety by grafting and budding onto rootstock shows that the foregoing and all other characteristics and distinctions come true to form and are established and transmitted through succeeding propagations.

The following is a detailed description of the new plum tree variety 'Queen Garnet', its flowers, foliage, and fruit based on observations of specimens grown at the Applethorpe Research Station on 'Nemared' and 'Golden Queen' peach rootstocks. Tree and leaf data measurements were obtained in January 2007 from a first group of trees planted in July 2001 and a second group of trees planted in July 2003. Fruit data measurements were obtained in January-February 2007 from the first group of trees planted in July 2001. The new plum tree variety 'Queen Garnet' and its fruit as described below may vary slightly in detail due to climate, soil conditions, and cultural practices under which the variety may be grown. Certain characteristics of this variety, such as growth and colour, may change with changing environmental conditions (e.g., light, temperature, moisture), nutrient availability, rootstocks, or other factors. The observations described herein are believed to apply to plants of the new plum tree variety 'Queen Garnet' grown under similar conditions of soil and climate elsewhere.

TREE

*Size.*—Moderate and in the medium range for a Japanese plum. Trees reach the desired pruning height of approximately 2 meters by the end of their third year of growth when they have a spread of approximately 1.5 meters.

*Vigour.*—Moderately vigorous and in the medium range for a Japanese plum. Responds typically to irrigation and fertiliser and can be grown on either 'Nemaguard', 'Nemared' or 'Golden Queen' peach rootstocks.

*Form.*—Semi-spreading.

*Density.*—Moderately dense in branching habit and in the medium range for a Japanese plum.

*Shape.*—Rounded.

*Productivity.*—Productive and requires fruit thinning to prevent limb breakage and to size fruit when cross pollinated with a suitable pollinisor, a plant that provides pollen in cross pollination.

*Fertility.*—Self unfruitful, requiring cross pollination by suitable early to mid-season blooming plum, such as 'Blackamber' or 'Santa Rosa';

*Bearing.*—Regular and uniform on both spurs and whips.

*Chilling requirement.*—Estimated to be approximately 700 chill units based on bloom time (flowering with 'Blackamber' plum).

Trunk:

*Size.*—Medium, attaining approximately 74 to 100 mm trunk diameter at a height of approximately 15 cm above the graft union at the end of about 3 years.

*Texture.*—Medium shaggy, developing some peeling bark.

*Color.*—Background colour of trunk: About Greyed-Purple 187A (RHS Fan 4, 1966). Lenticel colour: About Greyed-Orange 163A (RHS Fan 4, 1966).

Branches:

*Size.*—Terminal shoot growth from approximately 900 mm to 2 meters is common on bearing trees, averaging approximately 8 to 14 mm diameter at the base and approximately 2 mm diameter at the terminals as branches have long terminal growth giving the appearance of whippy fruiting branches.

*Texture.*—Smooth on new wood with a medium to large amount of lenticels developing on older wood, attaining size found on trunk and old scaffolds.

*Lenticels.*—Moderate number and in the medium range for Japanese plum and arranged horizontally on bark.

*Size.*—Approximately 2 to 4 mm long and approximately 0.5 to 1.0 mm wide on second year old wood.

*Colour.*—New wood is medium green, about Yellow-Green 144A (RHS Fan 3, 1966).

*Fruiting.*—Fruits on spurs and branches (whips).

LEAVES

*Arrangement.*—Alternate and horizontal attitude.

*Average size.*—Approximately 109 mm in length, approximately 45 mm in width and leaf petiole length approximately 14 mm.

*Form.*—Broad obovate.

*Apex.*—Pointed angle of tip.

*Base.*—Acute.

*Margin.*—Crenate with numerous small glands as seen at 10 times magnification. One gland on each tip of a saw tooth edge of the blade from base to tip. Not visible to naked eye.

*Thickness.*—Leaf thickness and coarseness is not, by touch, distinguishable from other varieties.

*Surface.*—Upper, reticulate; lower, medium veined.

*Texture.*—Glabrous.

*Petiole.*—Length: Approximately 14 mm. Diameter: Approximately 2 mm. Color: About Yellow-Green 146C (RHS, Fan 3, 1966).

*Petiole glands.*—About 2 to 3 small globose glands on upper portion of petiole or at base of leaf blade. Color about dark brown, about Greyed-Purple 183A (RHS Fan 4, 1966) on tips.

*Color.*—Upper leaf surface: Deep green, about Green 137A (RHS Fan 3, 1966). Lower leaf surface: Gray green, about Yellow-Green 147B (RHS Fan 3, 1966).

*Leaf vein color.*—Main vein on lower surface is about Yellow-Green 145C (RHS Fan 3, 1966).

FLOWER BUDS

*Size.*—Slightly shorter and thicker than leaf bud at the node.

*Length.*—Medium, approximately 2 mm.

*Diameter.*—Approximately 1 mm.

*Form.*—Ovate and free.

*Color.*—Brown, about Orange 26A (RHS Fan 1, 1966).

FLOWERS

*Blossom period.*—About 4 to 8 days. First Bloom varies from August 21 to September 2 (approximately 5% flowers open) and Full Bloom from August 25 to September 9 (approximately 75% flowers open) depending on seasonal conditions at Applethorpe.

*Size.*—Small to medium (approximately 25–27 mm diameter) flowers.

*Number of petals per flower.*—5.

*Petal size.*—Length: Approximately 11 to 12 mm length. Width: Approximately 6 to 7 mm width, with a smooth, wavy margin.

*Petal shape.*—Apex: Obtuse. Base: Cuneate.

*Petal color.*—White, about White 155D (RHS Fan 4, 1966).

*Pedicel.*—Length: Approximately 5 to 6 mm length. Diameter: Slightly less than approximately 1 mm diameter. Color: About Green 136D (RHS Fan 3, 1966).

*Pollen.*—Abundant, yellow, and functions well as a pollinisor, a male parent in cross-pollination.

*Scented.*—Strongly fragrant and pleasant.

*Anther colour.*—About Yellow-Orange (RHS Fan 1, 1966).

*Calyx cup.*—Medium size (approximately 6 mm diameter outside, approximately 3 mm deep inside below the petal base).

*Fertility.*—Requires cross-pollination for fruit set due to pollen self incompatibility.

FRUIT

General: Total fruit antioxidants ranges from approximately 23.2±12.3 mmoles ascorbic acid equivalents per gram flesh at picking ripe to approximately 27.9±4.67 mmoles ascorbic acid equivalents per gram flesh at eating ripe (about 7–10 days later). Anthocyanins measure from approximately 156±30.9 mg/100 grams at picking ripe to approximately 236±35.8 mg/100 grams at eating ripe.

*Maturity date.*—Yearly variable, but beginning February 8 to 21 at Applethorpe, and extending for up to about 3 weeks from first to last harvest.

*Weight.*—Averages approximately 114 grams, ranging from approximately 99 to 128 grams.

*Size.*—Length: Approximately 54 mm, ranging from approximately 51 to 59 mm. Diameter: Approximately 60 mm, ranging from approximately 57 to 63 mm.

*Form.*—Round to ovate.

*Suture.*—Inconspicuous line extending from base to the pistil point. Slightly furrowed at stem end and pistol point.

*Base.*—Slightly flat on shoulders.

*Apex.*—Slightly pointed.

*Cavity.*—Slight cavity at the apex of the seed in some fruit.

*Fruit stem.*—Length: Approximately 11 mm. Diameter: Approximately 1 to 1.5 mm. Color: Brown, about Greyed-Orange 166B (RHS Fan 4, 1966).

Flesh:

*Texture.*—Very firm, fine and chewy.

*Fibres.*—Small and not obvious.

*Flavor or eating quality.*—Sweet flesh with slightly tart skin.

*Juice.*—Very dark red, about Greyed-Purple 187A (RHS Fan 4, 1966). Total Soluble Solids (TSS) range from approximately 17 to 21%.

*Aroma.*—Moderately strong.

*Colour.*—Very dark red, about Greyed-Purple 187A (RHS Fan 4, 1966).

*Cavity.*—Some fruit have a cavity at tip end of endocarp (stone).

Skin:

*Thickness.*—Not unusually thick or thin for a typical Japanese plum.

*Texture.*—Not unusually coarse or smooth for a typical Japanese plum.

*Bloom (wax).*—Heavy and easily rubbed, leaving a shiny surface.

*Colour.*—Black and shiny, about Black 202A (RHS Fan 4, 1966).

*Taste.*—Balanced sweet/acid with some astringency.

*Lenticels.*—Many small covering nearly all of the fruit, approximately >30 per $cm^2$.

Stone:

*Type.*—Semi-freestone.

*Size.*—Length: Approximately 23 mm. Width: Approximately 17 mm.

*Form.*—Long elliptical, pointed pistil end with stalk end angle right-angle. Shape in ventral view is subglobular, shape in basal view is long elliptical.

*Sides.*—Profile asymmetric, Ventral symmetric.

*Surface.*—Small pits throughout and on blade.

*Ridges.*—Blade on suture extending about ⅓ length of stone.

*Color.*—Medium brown, about Greyed-Orange 164 A (RHS Fan 4, 1966).

*Tendency to split.*—No splitting observed.

Use:

Market. —Local and long distance for fresh dessert markets. Degree of firmness at harvest and firmness and flavor retained in refrigeration for about 28 days at 1° C. indicates fruit should be highly acceptable for shipping. Fruit is eminently suitable for processing because of firmness and extremely high anthocyanin levels compared to other Japanese plums.

Resistance to disease: No symptoms of bacterial spot on fruit, leaves and stems incited by *Xanthomonas campestris* pv. pruni (Sm.) Dye have been observed at Applethotpe.

Species: *Prunus salicinia.*

*Parentage.*—Female parent: 'Blackamber' (unpatented). Pollen parent: 'Amber Jewel' (unpatented).

What is claimed is:

1. A new and distinct plum tree named 'Queen Garnet' as herein described and illustrated.

* * * * *